(12) United States Patent
Holloway et al.

(10) Patent No.: US 6,500,123 B1
(45) Date of Patent: Dec. 31, 2002

(54) METHODS AND SYSTEMS FOR ALIGNING VIEWS OF IMAGE DATA

(75) Inventors: Richard Holloway, Chapel Hill; John J. Stefanski, Raleigh; Donald K. McAlister, Apex; Olaf von Ramm, Durham; David W. Smith, Raleigh; Stephen Michael Grenon, Hillborough, all of NC (US)

(73) Assignee: Volumetrics Medical Imaging, Durham, NC (US)

( * ) Notice: Subject to any disclaimer, the term of this patent is extended or adjusted under 35 U.S.C. 154(b) by 21 days.

(21) Appl. No.: 09/707,238

(22) Filed: Nov. 6, 2000

Related U.S. Application Data
(60) Provisional application No. 60/164,074, filed on Nov. 5, 1999.

(51) Int. Cl.[7] .................................................. A61B 8/00
(52) U.S. Cl. ...................................................... 600/443
(58) Field of Search .......................... 600/437, 441–447, 600/449–459; 128/916; 73/625, 626; 367/7, 11, 130, 138

(56) References Cited

U.S. PATENT DOCUMENTS 4,694,434 A  9/1987 von Ramm et al. ............ 367/7
5,546,807 A  8/1996 Oxaal et al. .................. 73/606

OTHER PUBLICATIONS http://www.3Dechotech.com, printed May 29, 2001, 7 pages.

http://www.tomtec.de, printed May 29, 2001, 3 pages.

*Primary Examiner*—Marvin M. Lateef
*Assistant Examiner*—Ali M. Imam
(74) *Attorney, Agent, or Firm*—Myers Bigel Sibley & Sajovec

(57) ABSTRACT

A first ultrasound dataset that represents an object in a first coordinate system can be acquired at a first time. Three landmarks of the object can be located in the first ultrasound dataset to define a second coordinate system. A first transform from the first to the second coordinate system can be determined for the first ultrasound dataset. A second ultrasound dataset that represents the object in the first coordinate system can be acquired at a second time. The same three landmarks in the second ultrasound dataset can be located to define a third coordinate system. A second transform from the first to the third coordinate systems can be determined for the second ultrasound dataset.

30 Claims, 6 Drawing Sheets

METHODS AND SYSTEMS FOR ALIGNING VIEWS OF IMAGE DATA

CROSS-REFERENCE TO RELATED APPLICATION

This application claims the benefit of Provisional Application No. 60/164,074 filed Nov. 5, 1999, entitled Volumetric Data Comparison System, the entire disclosure of which is incorporated herein by reference.

FIELD OF THE INVENTION

The present invention relates to the field of imaging in general, and more particularly, to ultrasound imaging.

BACKGROUND OF THE INVENTION

One common method of assessing the efficacy of a given treatment for a disease is to compare ultrasound images of an affected tissue both before and after the treatment. Unfortunately, it may be difficult to compare the 'before' and 'after' images if some of the affected tissue is not present in both images or if the images are not aligned with respect to each other.

In stress-echo type heart studies, portions of the heart can be scanned before and after a stress test to provide corresponding before and after images of selected portions of the heart. Unfortunately, it can be difficult to scan the same portions of heart in the before and after tests using current technology. In particular, it can be difficult to reliably scan the same portion of the heart using a two-dimensional (2D) ultrasound system (or scanner). For example, during the before scan, the 2D scanner may capture a single "slice" of a portion of the heart under investigation. It may be difficult for the operator to capture the same portion of the heart after the stress test because, for example, the patient is breathing harder or because the heart is beating faster and moving to a greater extent within the patient's body than before the stress test. This can mean that the before and after slices may not show the same portions of the heart and that a physician may have to mentally visualize the anatomy based on the differing 2D scans and correct for the differences between the before and after slices, which can be difficult.

SUMMARY OF THE INVENTION

Embodiments according to the present invention can provide methods and systems for aligning views of ultrasound data using transforms. Pursuant to these embodiments, a first ultrasound dataset that represents an object in a first coordinate system can be acquired at a first time. A plurality of landmarks of the object can be located in the first ultrasound dataset to define a second coordinate system. A first transform from the first to the second coordinate system can be determined for the first ultrasound dataset. A second ultrasound dataset that represents the object in the first coordinate system can be acquired at a second time. The same landmarks in the second ultrasound dataset can be located to define a third coordinate system. A second transform from the first to the third coordinate systems can be determined for the second ultrasound dataset.

By aligning the views, differences and similarities between the views may be readily observed, thereby possibly reducing the need to mentally visualize the anatomy, which can reduce the variability in diagnoses and lead to better treatment.

The present invention may allow two or more views of ultrasound image data to be aligned with respect to common anatomical features and display views of these features side by side while the stored data set is being recorded, is playing, or is paused, such as in a stress echo test. This may allow the user to directly compare ultrasound data acquired at different times, possibly from different locations and/or orientations. This may allow the data to be collected more quickly since the user may not have to examine as many views of the heart. Reducing the exam time may allow more patients to be seen in a day and help ensure that a stress echo test, taken after the patient's heart rate has been increased through exercise or drugs, can occur during peak heart rate.

In some embodiments according to the present invention, a first view of image data in the first ultrasound dataset is displayed in the second coordinate system using the first transform and a second view of image data in the second ultrasound dataset is displayed in the third coordinate system aligned with the first view using the second transform. In some embodiments according to the present invention, the first and second views are displayed on a single display. In still other embodiments, the first and second views do not include any of the landmarks.

The act of locating a plurality of landmarks of the object in the first ultrasound dataset can be performed by locating a first one of the landmarks in a first view of image data in the first ultrasound dataset and a second one of the landmarks in a second view of image data in the first ultrasound dataset that is different from the first view.

In other embodiments according to the present invention, a series of first views of image data in the first ultrasound dataset are displayed and a series of second views of image data in the second ultrasound dataset are displayed, wherein respective ones of the first views are aligned with respective ones of the second views.

In still other embodiments according to the present invention, the first view of image data has an associated first time within a cycle associated with the object and the second view of image data has an associated second time within the cycle that is different than the first time.

In still other embodiments according to the present invention, views of ultrasound data can be provided so that the views appear to have been acquired from a different location and/or orientation. Pursuant to these embodiments, an object can be scanned to provide an ultrasound dataset that represents the object in a first coordinate system. A second coordinate system can be determined that is different than the first coordinate system. A transform can be determined for image data in the ultrasound dataset from the first coordinate system to the second coordinate system. A view of image data in the ultrasound dataset in the second coordinate system can be displayed using the transform. In some embodiments according to the present invention, the transform can be determined by locating at least three landmarks of the object in the ultrasound dataset.

In further embodiments according to the present invention, the transform can be changed based on user input to provide a second transform and a second view of image data in the ultrasound dataset which can be displayed using the second transform. In some embodiments, the user input can be provided via a trackball or other type of input device. In still other embodiments, an instrument can be guided in a body that contains the object based on the view while scanning is performed.

DETAILED DESCRIPTION OF EMBODIMENTS OF THE INVENTION

Figure 1:
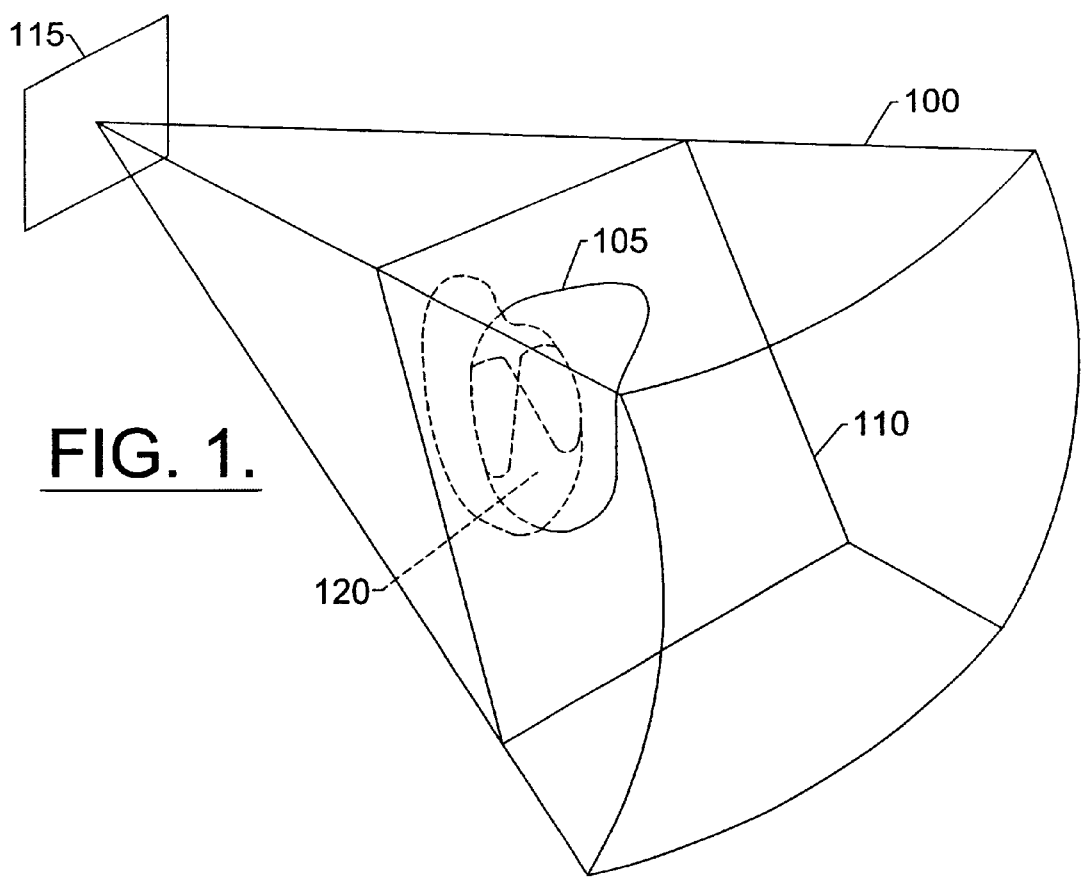
FIG. 1 is a schematic diagram that illustrates scanning of volumes including objects to be studied.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Embodiments according to the present invention are described herein with reference to ultrasound modalities. It will be understood, however, that the present invention may be utilized with other imaging modalities such as Magnetic Resonance Imaging (MRI) and Computerized Tomography (CT). Furthermore, although the present invention is described by reference to echocardiography and stress-echo testing, the present invention can be utilized in numerous other types of studies, such as biopsy or other types of guidance-related procedures.

Although the present invention is described herein with reference to ultrasound systems that scan volumes to provide 3D ultrasound datasets, it will be understood that the present invention may be utilized with ultrasound systems that scan in two dimensions to provide 2D ultrasound datasets. The components of the ultrasound systems described herein may be packaged as a single unit or packaged separately and interconnected to provide embodiments of methods and systems according to the present invention.

As used herein, the term "tissue" includes blood and organs, such as a heart, found in a biological body. Although embodiments according to the present invention are disclosed herein in reference to the scanning of tissue, it will be understood that the present invention may be utilized to scan other objects. Although the present invention is described herein as being used to compare ultrasound images, it will be understood that the present invention may be utilized to compare color flow or power mode data.

As will be appreciated by those of skill in the art, the present invention may be embodied as methods and/or systems. Accordingly, the present invention may take the form of hardware embodiments, software embodiments or embodiments that combine software and hardware aspects.

The present invention is disclosed using flowchart illustrations. It will be understood that blocks of the flowchart illustrations, and combinations of blocks, can be implemented by computer program instructions. These program instructions may be provided to a processor circuit(s), such as a Digital Signal Processor (DSP) circuit, within an ultrasound system according to the present invention, such that the instructions which execute on the processor circuit(s) create means for implementing the functions specified in the block or blocks. The computer program instructions may be executed by the processor circuit(s) to cause a series of operational steps to be performed by the processor circuit(s) to produce a computer implemented process such that the instructions which execute on the processor circuit(s) provide steps for implementing the functions specified in the block or blocks.

Accordingly, the blocks support combinations of means for performing the specified functions, combinations of steps for performing the specified functions and program instructions for performing the specified functions. It will also be understood that each block, and combinations of blocks, can be implemented by special purpose hardware-based systems which perform the specified functions or steps, or combinations of special purpose hardware and computer instructions.

According to embodiments of the present invention, views of an object, such as a heart, can be aligned to provide for easier comparison of the views. The views can be aligned by determining transforms from a first coordinate system to a second coordinate system for at least one of the views to be compared. The transform(s) can allow image data from two or more acquired ultrasound datasets to be transformed to a common coordinate system so that the views of image data may be aligned.

According to FIG. 1, an ultrasound scanner (or system), such as those described for example in U.S. Pat. No. 4,694,434 to von Ramm et al. (Von Ramm) entitled Three Dimensional Imaging System and U.S. Pat. No. 5,546,807 to Oxaal et al. (Oxaal) entitled High Speed Volumetric Ultrasound Imaging System, the entire disclosures of which are incorporated herein by reference, can be used to scan a volume 100 using a transducer 115 to acquire 3D ultrasound datasets that represent an object or objects within the volume 100. The 3D ultrasound dataset can include image data generated from echoes of ultrasound beams reflected from the object(s) in the volume 100. Accordingly, the 3D ultrasound dataset can be a 'snapshot' of the object in the volume 100 at a particular time. The volume 100 can include tissue, such as a heart 105, or other objects to be studied. A series of snapshots of the volume 100 can be acquired at a series of respective times. For example, the system may acquire one snapshot every 0.05 seconds over an entire cycle of the heart 105. The snapshots can be stored for later examination.

Figure 2:
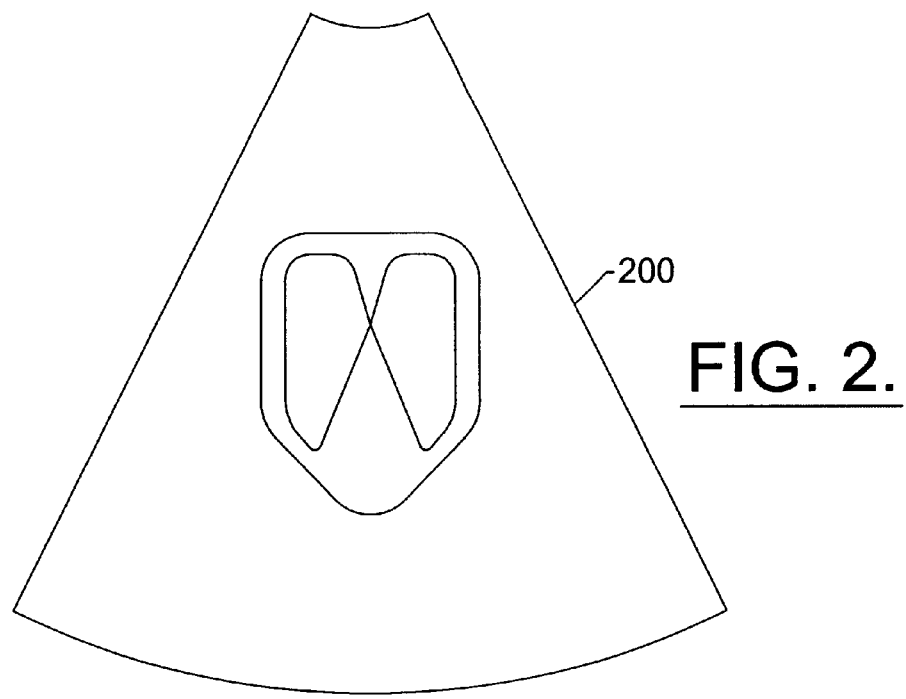
FIG. 2 is a schematic diagram of a view of a slice of an object in a scanned volume.

The ultrasound system may include means for displaying views of the acquired image data included in the 3D ultrasound dataset. The views can be 'slices' of the tissue in volume 100. For example, the system can provide a view 200 of a slice 110 that passes through the heart 105 as indicated by the dotted line 125 as shown in FIG. 1. As shown in FIG. 2, the view 200 can be a 2D view of the image data that corresponds to area 120 where the slice 110 intersects the heart 105 (see FIG. 1). The system can provide the view 200 by selecting image data from the 3D ultrasound dataset that lies on or within the slice 110 as disclosed in Oxaal.

It will be understood that the slice 110 can be an Inclined (I) slice, a Constant depth (C) slice, a B-mode slice, or any other type of cross-section of the tissue at any orientation. For example, the slice 110 is inclined or 'tilted' within the volume 100.

Figure 3:
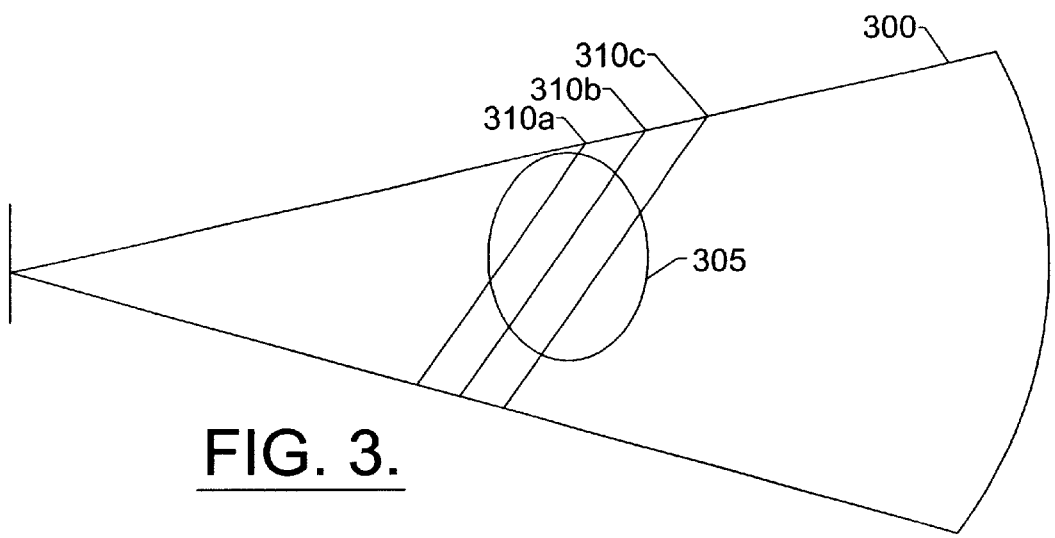
FIG. 3 is a schematic diagram of a side view of slices of an object in a scanned volume.

As shown in FIG. 3, the view can be changed to display different slices 310*a–c*. For example, the user may desire to see the different views 310*a–c* of the image data from the 3D ultrasound dataset that correspond to the different depths of an object 305. As disclosed in Oxaal, the system may need to scan the volume 300 only one time to acquire the 3D ultrasound dataset. Thereafter, the system can provide the different views 310*a–c* by selecting the image data that corresponds to the slices 310*a–c* without requiring any further scans.

Figure 4:
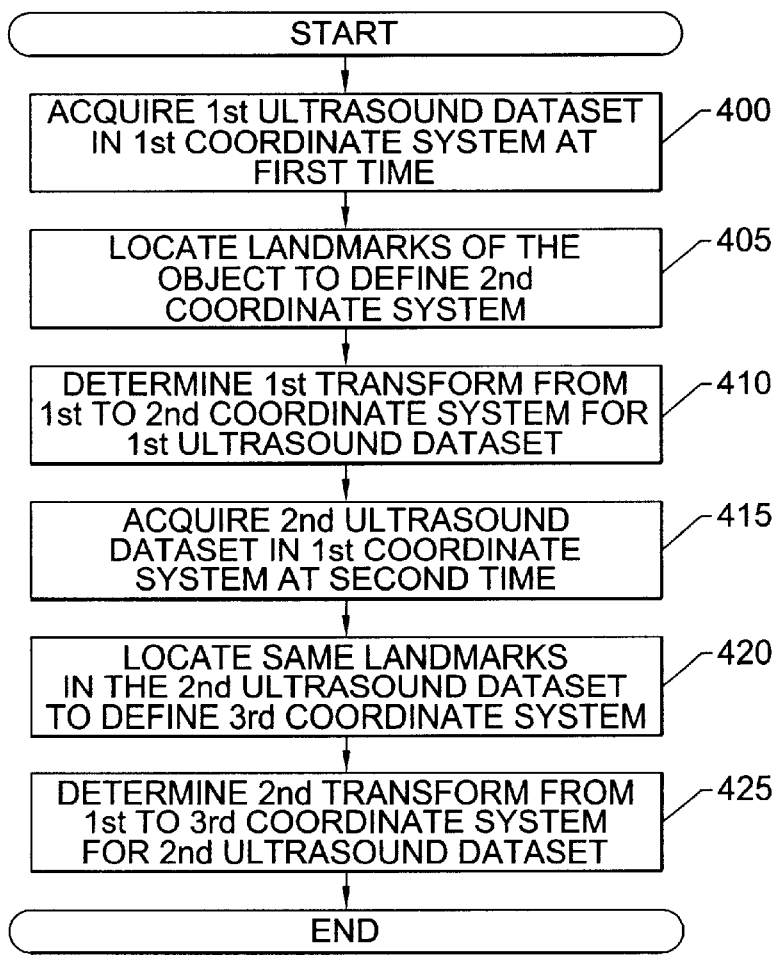
FIG. 4 is a flowchart that illustrates embodiments of methods and systems according to the present invention.

FIG. 4 is a flowchart that illustrates methods and systems according to the present invention. According to FIG. 4, a first 3D ultrasound dataset is acquired (block 400). The first 3D ultrasound dataset can represent an object in a first coordinate system at a first time. The first coordinate system can be defined to be any coordinate system that is convenient, such as a coordinate system defined with respect to a transducer used to acquire the first 3D ultrasound dataset. A plurality of landmarks (typically three) of the object in the first 3D ultrasound dataset can be located (block 405). For example, the user may examine a series of views of the image data included in the first 3D ultrasound dataset to locate a top landmark, a sidewall landmark, and a bottom landmark of the heart. It will be understood that the landmarks can be any features of the object that the user can distinguish when examining views of the object being studied.

The landmarks can be located by viewing different views of the image data. For example, the user may select three different views where a single landmark is located in each of the different views. Alternatively, two of the three landmarks may be located to define an axis around which a view can be rotated to locate the third landmark. The positions of the top, side, and bottom landmarks of the object in the first 3D ultrasound data can be used to define a second coordinate system.

A first transform from the first to the second coordinate system can be determined (block 410). Accordingly, image data included in the first 3D ultrasound dataset can be mapped from the first to the second coordinate system using the first transform.

A second 3D ultrasound dataset can be acquired (block 415). The second 3D ultrasound dataset may represent the object at a second time. The first coordinate system can be the same coordinate system defined for the first 3D ultrasound dataset. For example, the second 3D ultrasound dataset can be acquired by the same transducer that was used to acquire the first 3D ultrasound dataset. The first and second 3D ultrasound datasets can be acquired in real time or can be acquired from a device that is used to store the first and second 3D ultrasound datasets after scanning the object.

The same landmarks located in the first 3D ultrasound dataset can be located in the second 3D ultrasound dataset (block 420). These landmarks may be used to define a third coordinate system. A second transform from the first to the third coordinate system can be determined (block 425). The second transform can be used to map image data in the second 3D ultrasound dataset from the first coordinate system to the third coordinate system. In other embodiments, a different set of landmarks are located in the second 3D ultrasound dataset.

Accordingly, the image data from the first and second 3D ultrasound datasets needed for the desired views can be mapped to a common coordinate system. Displaying the first and second views in the common coordinate system can make it appear that the image data in the first and second views was acquired by a transducer in the same location.

Figure 5:
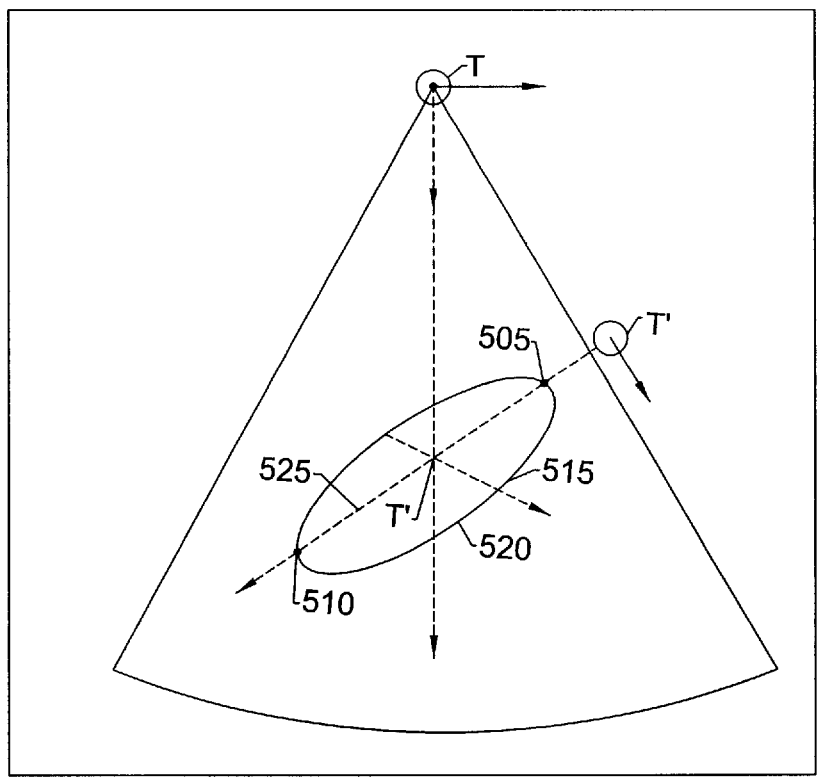
FIG. 5 is a schematic diagram of a view of ultrasound image data that illustrates embodiments of methods and systems according to the present invention.

FIG. 5 is a diagram that illustrates embodiments of methods and systems according to the present invention. According to FIG. 5, an ultrasound system can be used to acquire first and second 3D ultrasound datasets at first and second times respectively. Each of the first and second 3D ultrasound datasets can include image data that corresponds to the tissue that was scanned. In one embodiment, the first and second 3D ultrasound datasets represent 'before' and 'after' scans of a heart in a stress-echocardiography (stress-echo) test.

The user can view a series of different views 500, such as the view in FIG. 5, in order to locate three landmarks of an object 520 in the volume. For simplicity, FIG. 5 shows a single slice 500 that includes all three landmarks. The user may sweep through the first 3D ultrasound dataset in an azimuth direction to locate the first two landmarks and sweep through an elevation direction to locate the third landmark. Other techniques can be used to locate the landmarks. Furthermore, more than three landmarks can be used to align the views. It will also be understood that two landmarks may be used to align the views where, for example, the first and second ultrasound datasets are 2D rather than 3D.

The image data in the series of views can be displayed in a first coordinate system, T. The coordinate system T may be defined, for example, with respect to a transducer that is used to acquire the first 3D ultrasound dataset, or can be defined with respect to some other reference.

The three landmarks can be used to define a second coordinate system, T', for the first 3D ultrasound dataset. For example, the landmarks can include a top landmark 505, a bottom landmark 510, and a side landmark 515. The top landmark 505 and the bottom landmark 510 can be used to define an axis 525 that passes through the top landmark 505 and the bottom landmark 510. The origin of T' can be defined arbitrarily relative to the axis 525. The side landmark 515 can be used to define a reference plane that includes the axis 525 and the side landmark 515. Other techniques can be used to define the second coordinate system T'.

Figure 6:
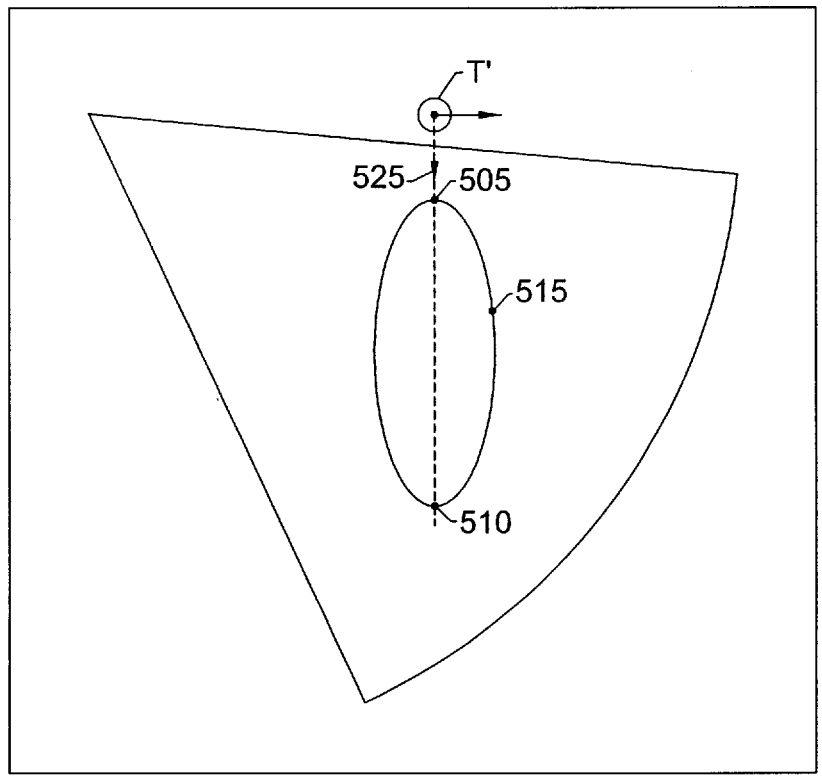
FIG. 6 is a schematic diagram of a view of ultrasound image data that illustrates embodiments of methods and systems according to the present invention.
Figure 7:
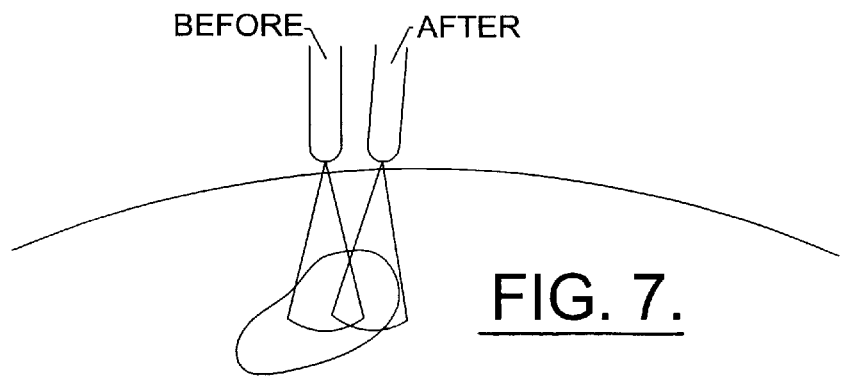
FIG. 7 is a schematic diagram of a view of ultrasound image data that illustrates scans performed from different location and/or orientations.

A first transform can be determined to perform the mapping discussed above. In particular, the first transform can map image data from the coordinate system T to the coordinate system T'. Accordingly, when a view of a slice of an object is to be displayed, the image data needed for the slice can be transformed so that the view of the slice appears from the perspective of the coordinate system T'. For example, the perspective of the coordinate system T' might make the view appear that the scan was performed by a transducer that was located along the axis 525 as shown in FIG. 6. In this example, the first transform can be used to map image data from the first 3D ultrasound dataset so that the top landmark 505 and the bottom landmark 510 are vertically aligned in the center of the view 600. The first transform can be a rigid-body transform that provides for rotation and translation of the image data. Other types of transforms, such as warping transforms, could also be used to map the data.

A second transform can be determined to map image data in the second 3D ultrasound dataset to a coordinate system T". The coordinate system T" for the second 3D ultrasound dataset can be defined using the same landmarks of the object that were used in determining the transform for the first 3D ultrasound dataset. For example, the user can display a series of views of the image data in the second 3D ultrasound dataset to find the top, bottom, and side landmarks 505, 510, 515. The coordinate system T" for the second 3D ultrasound dataset can be defined using the three landmarks as disclosed above in reference to the first 3D ultrasound dataset. Furthermore, the second transform, that maps image data from the second 3D ultrasound dataset to the coordinate system T", can be determined as disclosed above in reference to the first 3D ultrasound dataset.

It will be understood that the alignment may be performed so as to substantially align the views so that an effective comparison may be made. Accordingly, the views may not need to be precisely aligned to provide for the comparison. For example, the landmarks chosen in the before and after views may be slightly offset from one another due to operator error or system convenience. Alternatively, the shape of the object may have changed in the time interval between when before and after scans were performed. For example, the patient's heart may have become enlarged after the stress test. Furthermore, the alignment may be improved using data correlation techniques to adjust the transform to compensate for differences in landmark selection and/or processing by the system.

It also will be appreciated that in some circumstances there may be no need to transform the image data in the first 3D ultrasound dataset from a first coordinate system to a second coordinate system. Instead, the image data in the second 3D ultrasound dataset may be transformed from its original coordinate system to the coordinate system of the image data in the first 3D ultrasound dataset. Accordingly, it will be appreciated that in certain embodiments of the present invention only a single transform may be needed to align views from two different 3D ultrasound datasets for viewing.

In contrast, some conventional systems may not have the capability to align before and after slices if the transducer placement changes between when the first and second scans the views provided. Accordingly, the views of slices of the heart that a conventional system may provide can appear differently, due, for example, to different transducer placements in performing the before and after scans.

Figure 8A:
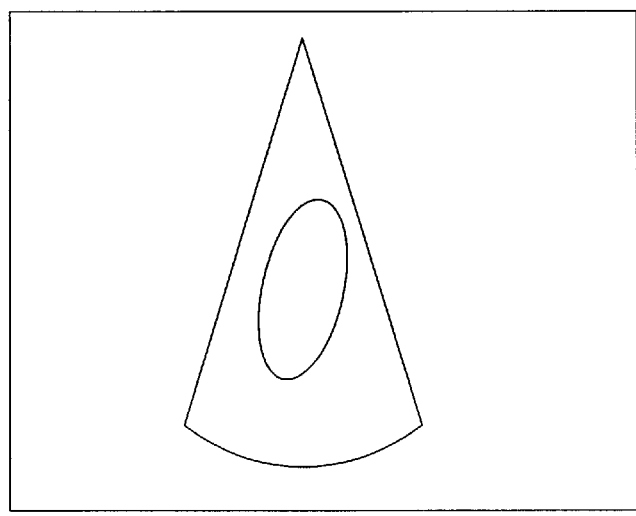
FIGS. 8A and 8B are schematic diagrams of views of ultrasound image data that illustrate scans that appear to have been performed from the same location and/or orientation relative to an object of interest according to embodiments of the present invention.
Figure 8B:
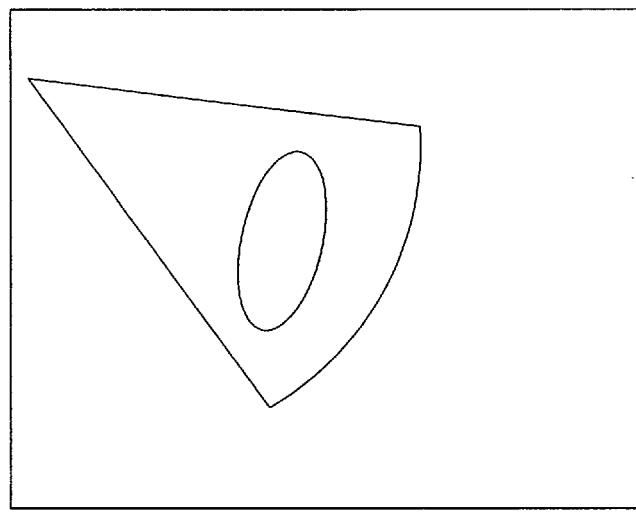

The first and second transforms can be applied, for example, to before and after 3D ultrasound datasets acquired as part of stress-echo testing to align the before and after views of the heart. The aligned views can make it appear as if the image data was acquired using the same transducer location and orientation for both scans. For example, as shown in FIGS. 8A and 8B, embodiments according to the present invention can be used to make the views appear to have been generated based on scans performed from the same position. Aligning the before and after views can make comparing the views easier and can improve the accuracy of a diagnosis based on the stress-echo test.

Figure 9:
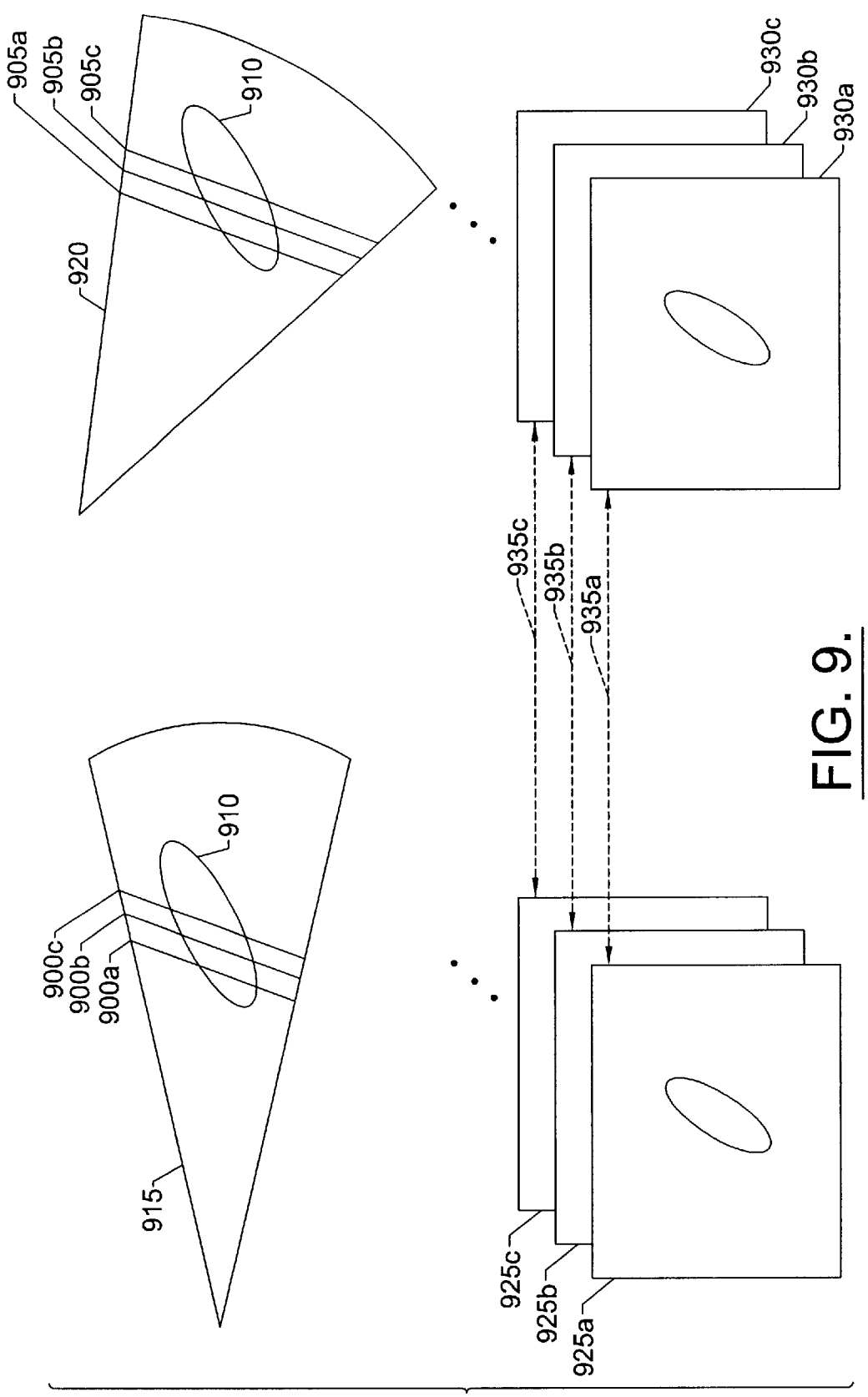
FIG. 9 is a schematic diagram that illustrates series of first and second aligned views having corresponding locations in the first and second ultrasound datasets respectively.

A series of aligned views may also be provided for each of the first and second 3D ultrasound datasets as shown, for example, in FIG. 9. According to FIG. 9, a first scan can provide a first snapshot 915 of an object 910 that include a series of first slices 900a–c of the object 910, where each of the first slices 900a–c corresponds to a different depth in the object 910. A second scan can provide a second snapshot 920 that includes a series of second slices 905a–c, where each of the second slices 905a–c corresponds to the same depths in the object 910 as the first slices 900a–c.

A series of first views 925a–c corresponding to the series of first slices 900a–c can be displayed. A series of second views 930a–c corresponding to the series of second slices 905a–c can also be displayed. The first views 925a–c and the second views 930a–c can be 'locked' to one another so that the same transform, relative to a coordinate system 940, may be applied to provide both views of the image data as illustrated by the dotted lines 935a–c. For example, as shown in FIG. 9, each of the first views 925a–c can be locked to each of the second views 930a–c respectively. As the transform is incrementally changed from providing the view 925a to 925b, the same increment can be applied to the transform used to provide the change from the view 930a to 930b. Locking the views to one another can, therefore, help to ensure that the views are aligned as the user switches from one view to the next view in the series. It will be understood that locking the views can also be applied to changing the tilts associated with the views as well as the depth as described above.

It will be understood that the views may also be independent so that, for example, the user may specify the alignment for each view. For example, in a stress-echo test, the before view may have a different orientation than the after view. The views can also be displayed side-by-side, for example, on a single display to ease the comparison of the two views.

In some conventional systems, a user may not be able to compare views of arbitrary slices of the volume scanned because the conventional system may only scan what is displayed. For example, in some conventional systems, the only two views that may be compared are the before and after views that include all of the landmarks. In contrast, according to the present invention, any of the image data included in the 3D ultrasound datasets can be transformed to provide a view of the desired slice, even though the desired slices may not have been viewed as the scans were performed.

Furthermore, the aligned views can be provided for any arbitrary slices to be viewed. In particular, the transforms can be applied to any image data in the 3D ultrasound datasets to display the views of any of the slices that a user may wish to view. For example, the user may wish to compare slices of the heart that were viewed during scanning. Moreover, the views chosen to be aligned can be of slices that do not include any of the landmarks used to align the views.

The transforms used to align the views can be changed to compensate for different movements between the first and second views. For example, in a stress test, the patient's heart may beat harder after the stress test than before. Accordingly, the heart may move to a greater extent within the patient's chest during scanning after the stress test. The transform used to align the 'after' view of the heart with the before view can be changed to provide for an alignment on a snapshot-by-snapshot basis. For example, as the heart moves over a relatively large distance in the chest, the transform may need to be changed for each snapshot to provide a view that is aligned with the corresponding view of the heart before the stress test.

The views can also have associated times within cycles associated with the object being scanned. For example, in studies of the heart, each of the views included in the series of first views can have a time associated therewith. Similarly, each of the views included in the series of second views can have a time associated therewith. The comparisons of the views may be further improved by comparing the views that have approximately the same times associated therewith.

It will be understood that the time associated with cycles of the object can include phases of operation of the object. For example, in studies of the heart, each view of the heart can have a Q, R, S, or T phase of heart operation associated therewith. The before and after views having the same, or approximately the same, phases of operation can be aligned and compared despite having different times associated with each. Moreover, views may be interpolated or extrapolated from other views to provide, for example, estimated views of operations of the object that were not captured in the scan.

Figure 10:
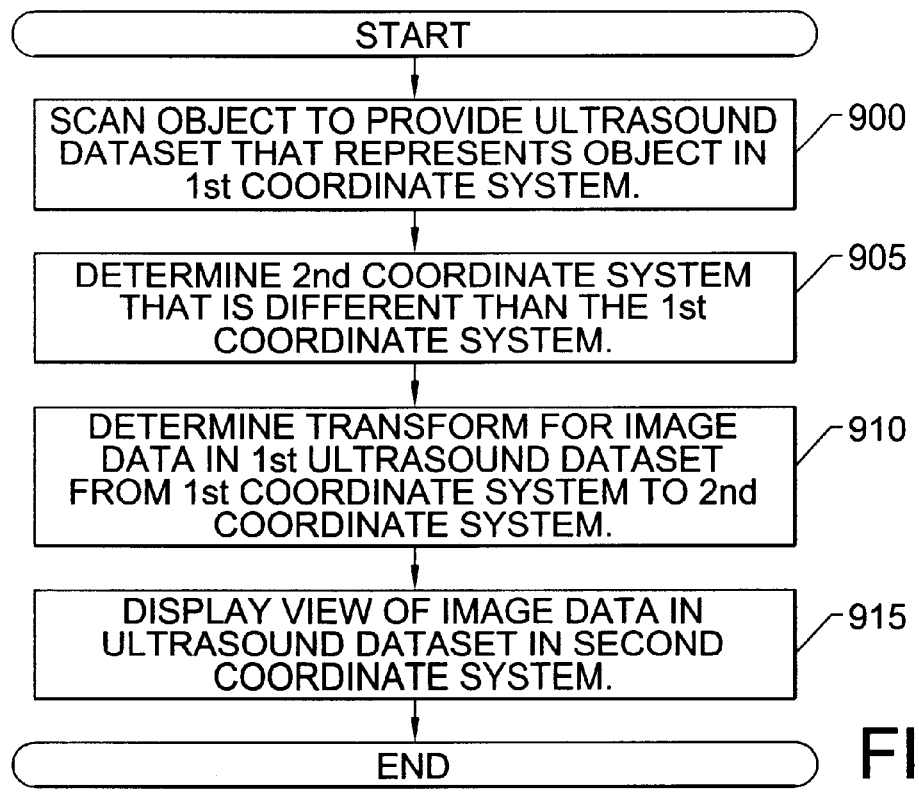
FIG. 10 is a schematic diagram of a view of ultrasound image data that illustrates scans from inconvenient and/or unusual positions and/or orientations during a procedure.

Pursuant to other embodiments of methods and system according to the present invention, transformed views of ultrasound data can be displayed while scanning. According to FIG. 10, transformed views of ultrasound data can displayed by scanning an object to provide a 3D ultrasound dataset that represents the object in a first coordinate system (block 900). A second coordinate system, different than the first coordinate system, may then be determined (block 905). A transform can be determined that transforms image data from the first coordinate system to the second coordinate system (block 910). A view of image data in the 3D ultrasound dataset is displayed in the second coordinate system using the transform (block 915). Accordingly, a view of image data can be transformed from the first coordinate system in which the image data was acquired to the second coordinate system which may provide a more natural view of the image data.

Figure 11:
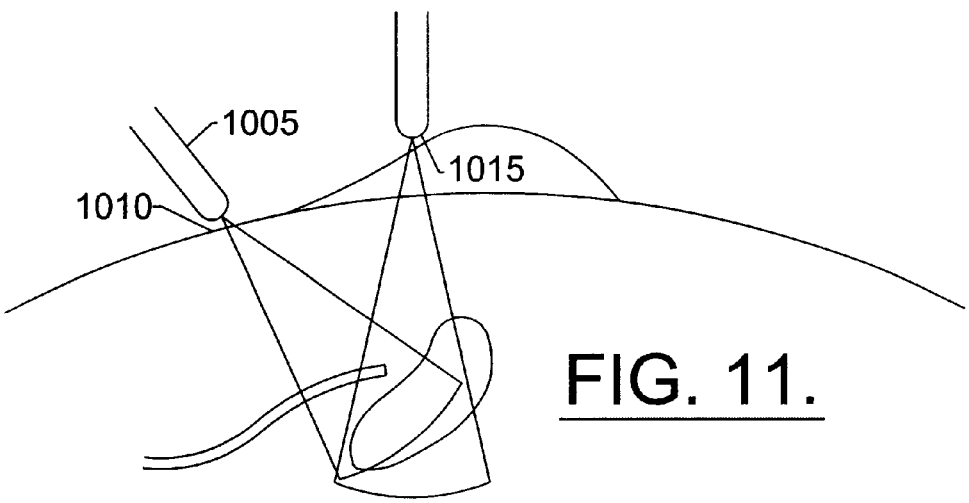
FIG. 11 is a schematic diagram of a view of ultrasound image data that illustrates scans that appear to have been performed from a different location during a procedure according to embodiments of the present invention.

As shown in FIG. 11, during a procedure, such as an in vivo study of a fetus, an instrument, such as a biopsy needle guided from outside the body, may be guided to the fetus using an ultrasound system that provides images in real time. According to embodiments of the present invention, views of image data provided by a transducer 1005 in a position 1010 can be transformed to make it appear that the image data was acquired from a different position 1015. Transforming the view, as discussed above, may provide a more intuitive image to aid in the guidance of the instrument.

As the position of the object being studied or the instrument changes, the transform can be changed to change the view so that the display may remain stable or so that a new view of the image data can be provided. The transform may be changed in response to manipulation, for example, of a trackball. Other types of input devices may be used. The changes to the transform may, therefore, be incremental.

Embodiments according to the present invention may, therefore, provide views of ultrasound data that appear to have been acquired using a transducer that was located in a different position. Transforming the view in this way may provide for improved views of the object, for example, during a procedure that involves guidance of an instrument relative to the object or when an object may not be scanned from a conventional location and/or orientation.

An exemplary derivation of a transform matrix according to embodiments of the present invention will now be described in further detail with reference to FIGS. 5 and 6.

In particular, the axis 525 is to appear centered and vertical in the view 600 of FIG. 6. Assuming that P1 is the top landmark 505, P2 is the bottom landmark 510, and P3 is side landmark 515, the normalized y-axis direction vector for T' can be expressed as:

$$Y_{T\_V'} = (V_{T\_P2} - V_{T\_P1}) / \|V_{T\_P2} - V_{T\_P1}\| \quad (1)$$

Then a vector from the view V to the side landmark 515 can be expressed in T' as:

$$V_{V\_P3} = V_{T\_P3} - V_{T\_V} \quad (2)$$

A unit z-axis direction vector for T' can be expressed as $$Z_{T\_V'} = (V_{V\_P2} \otimes V_{V\_P3}) / \|V_{V\_P2} \otimes V_{V\_hd\,P3}\| \quad (3)$$

where '$\otimes$' indicates a vector cross product. A unit x-axis direction vector for T' can be expressed as:

$$X_{T\_V'} = Y_{T\_V'} \otimes Z_{T\_V'} \quad (4)$$

The rotation matrix that expresses the rotation of V' with respect to T is:

$$R_{T\_V'} = [X_{T_{hd}\_V'}{}^T, Y_{T\_V'}{}^T, Z_{T\_V'}{}^T] \quad (5)$$

where the unit axis vectors form the columns of $R_{T\_V'}$.

The translation vector from T to V is:

$$V_{T\_V'} = V_{T\_M} - S_{T\_V'} * R_{T\_V'} * V_{V\_C} \quad (6)$$

where $V_{T\_M} = (V_{T\_P1} + V_{T\_P2})/2$, $S_{T\_V'}$ is a scale factor to convert from image data to samples, and $V_{V\_C} = (w/2, h/2)$ where w and h are the width and height of the view 600.

The transform matrix can be expressed as:

$$M_{T\_V'} = [R_{T\_V'} | V_{T\_V'}{}^T] \quad (7)$$

$M_{T\_T'}$ is computed as:

$$M_{T\_T'} = M_{T\_V'} * M_{V0\_T} \quad (8)$$

where $M_{V0\_T}$ is the untilted view 600 in its canonical location. This can make the z axis of T' coordinate system pass through the top landmark 505 and the bottom landmark 510. This transform matrix is can be applied to all views via:

$$M_{T'\_V} = M_{T'\_T} * M_{T\_V} \quad (9)$$

It will also be understood that the transform matrix can be used to modify any geometric representation of the volume, including, but not limited to, volume renderings, surface renderings, wire-mesh renderings, and interpenetrating cut planes.

In the drawings and specification, there have been disclosed typical preferred embodiments of the invention and, although specific terms are employed, they are used in a generic and descriptive sense only and not for purposes of limitation, the scope of the invention being set forth in the following claims. Other systems and computer program products may also be claimed.

What is claimed:

1. A method for aligning views of ultrasound data, the method comprising:

acquiring a first ultrasound dataset that represents an object in a first coordinate system at a first time;

locating a plurality of landmarks of the object in the first ultrasound dataset to define a second coordinate system;

determining a first transform function from the first to the second coordinate system for the first ultrasound dataset;

acquiring a second ultrasound dataset that represents the object in the first coordinate system at a second time;

locating the plurality of landmarks in the second ultrasound dataset to define a third coordinate system; and determining a second transform function from the first to the third coordinate systems for the second ultrasound dataset.

2. A method according to claim 1, wherein the second and third coordinate systems are aligned.

3. A method for aligning views of ultrasound data, the method comprising:

acquiring a first ultrasound dataset that represents an object in a first coordinate system at a first time;

locating a plurality of landmarks of the object in the first ultrasound dataset to define a second coordinate system;

determining a first transform function from the first to the second coordinate system for the first ultrasound dataset;

acquiring a second ultrasound dataset that represents the object in the first coordinate system at a second time;

locating the plurality of landmarks in the second ultrasound dataset to define a third coordinate system; and determining a second transform function from the first to the third coordinate systems for the second ultrasound dataset, the method further comprising:

displaying a first view of image data in the first ultrasound dataset in the second coordinate system using the first transform; and displaying a second view of image data in the second ultrasound dataset in the third coordinate system aligned with the first view using the second transform.

4. A method for aligning views of ultrasound data, the method comprising:

acquiring a first ultrasound dataset that represents an object in a first coordinate system at a first time;

locating a plurality of landmarks of the object in the first ultrasound dataset to define a second coordinate system;

determining a first transform function from the first to the second coordinate system for the first ultrasound dataset;

acquiring a second ultrasound dataset that represents the object in the first coordinate system at a second time;

locating the plurality of landmarks in the second ultrasound dataset to define a third coordinate system; and determining a second transform function from the first to the third coordinate systems for the second ultrasound dataset, wherein the act of locating the plurality of landmarks of the object in the first ultrasound dataset comprises locating a first one of the three landmarks in a first view of image data in the first ultrasound dataset and a second one of the three landmarks in a second view of image data in the first ultrasound dataset that is different from the first view.

5. A method according to claim 3, wherein the first view of image data has an associated first time within a cycle associated with the object and the second view of image data has an associated second time within the cycle that is different than the first time.

6. A method according to claim 3, wherein the first and second views do not include any of the plurality of landmarks.

7. A method according to claim 3 further comprising: comparing the first and second views.

8. A method according to claim 3, wherein the first and second views are displayed simultaneously.

9. A method according to claim 3 further comprising: displaying the first and second views on a single display.

10. A method for aligning views of ultrasound data, the method comprising:

acquiring a first ultrasound dataset that represents an object in a first coordinate system at a first time;

locating a plurality of landmarks of the object in the first ultrasound dataset to define a second coordinate system;

determining a first transform function from the first to the second coordinate system for the first ultrasound dataset;

acquiring a second ultrasound dataset that represents the object in the first coordinate system at a second time;

locating the plurality of landmarks in the second ultrasound dataset to define a third coordinate system; and determining a second transform function from the first to the third coordinate systems for the second ultrasound dataset, the method further comprising:

displaying a series of first view of image data in the first ultrasound dataset; and displaying a series of second views of image data in the second ultrasound dataset, wherein respective ones of the first views are aligned with respective ones of the second views.

11. A method for aligning views of ultrasound data, the method comprising:

acquiring a first ultrasound dataset that represents an object in a first coordinate system at a first time;

locating a plurality of landmarks of the object in the first ultrasound dataset to define a second coordinate system;

determining a first transform function from the first to the second coordinate system for the first ultrasound dataset;

acquiring a second ultrasound dataset that represents the object in the first coordinate system at a second time;

locating the plurality of landmarks in the second ultrasound dataset to define a third coordinate system; and determining a second transform function from the first to the third coordinate systems for the second ultrasound dataset, the method further comprising:

displaying a series of first views of image data from the first ultrasound dataset that correspond to respective locations in the object; and displaying a series of second views of image data from the second ultrasound dataset that correspond to the same locations in the object, wherein respective ones of the first and second views are aligned.

12. A method for aligning views of ultrasound data, the method comprising:

acquiring a first ultrasound dataset that represents an object in a first coordinate system at a first time;

locating a plurality of landmarks of the object in the first ultrasound dataset to define a second coordinate system;

determining a first transform function from the first to the second coordinate system for the first ultrasound dataset;

acquiring a second ultrasound dataset that represents the object in the first coordinate system at a second time;

locating the plurality of landmarks in the second ultrasound dataset to define a third coordinate system; and determining a second transform function from the first to the third coordinate systems for the second ultrasound dataset, wherein the object comprises tissue.

13. A method for aligning views of ultrasound data, the method comprising:

acquiring a first ultrasound dataset that represents an object in a first coordinate system at a first time;

locating a plurality of landmarks of the object in the first ultrasound dataset to define a second coordinate system;

determining a first transform function from the first to the second coordinate system for the first ultrasound dataset;

acquiring a second ultrasound dataset that represents the object in the first coordinate system at a second time;

locating the plurality of landmarks in the second ultrasound dataset to define a third coordinate system; and determining a second transform function from the first to the third coordinate systems for the second ultrasound dataset, wherein the plurality of landmarks comprises at least three landmarks.

14. A method for aligning views of ultrasound data, the method comprising:

acquiring a first ultrasound dataset that represents an object at a first time;

acquiring a second ultrasound dataset that represents the object at a second time; locating a plurality of first landmarks of the object in the first ultrasound dataset;

locating a plurality of second landmarks of the object in the second ultrasound dataset; and transforming image data, using a transform function, from the first ultrasound dataset to the second ultrasound dataset to align the plurality of first landmarks in the first ultrasound dataset with the plurality of second landmarks in the second ultrasound dataset.

15. A method according to claim 14, wherein the plurality of first landmarks and the plurality of second landmarks are the same.

16. A method according to claim 14, wherein the plurality of first landmarks comprises at least three landmarks.

17. A method for aligning views of ultrasound data, the method comprising:

acquiring a first ultrasound dataset that represents an object at a first time;

acquiring a second ultrasound dataset that represents the object at a second time;

locating a plurality of first landmarks of the object in the first ultrasound dataset;

locating a plurality of second landmarks of the object in the second ultrasound dataset; and transforming image data, using a transform function, from the first ultrasound dataset to the second ultrasound dataset to align the plurality of first landmarks in the first ultrasound dataset with the plurality of second landmarks in the second ultrasound dataset, wherein the first ultrasound dataset has an associated first coordinate system and the second ultrasound dataset has an associated second coordinate system; and wherein the act of transforming comprises transforming image data from the second coordinate system to the first coordinate system.

18. A system for aligning views of ultrasound data, the system comprising:

means for acquiring a first ultrasound dataset that represents an object in a first coordinate system at a first time;

means for locating a plurality of landmarks of the object in the first ultrasound dataset to define a second coordinate system;

means for determining a first transform function from the first to the second coordinate system for the first ultrasound dataset;

means for acquiring a second ultrasound dataset that represents the object in the first coordinate system at a second time;

means for locating the plurality of landmarks in the second ultrasound dataset to define a third coordinate system; and means for determining a second transform function from the first to the third coordinate systems for the second ultrasound dataset.

19. A system according to claim 18, wherein the second and third coordinate systems are aligned.

20. A system according to claim 18, wherein the object comprises tissue.

21. A system according to claim 18, wherein the plurality of landmarks comprises at least three landmarks.

22. A system for aligning views of ultrasound data, the system comprising:

means for acquiring a first ultrasound dataset that represents an object in a first coordinate system at a first time;

means for locating a plurality of landmarks of the object in the first ultrasound dataset to define a second coordinate system;

means for determining a first transform function from the first to the second coordinate system for the first ultrasound dataset;

means for acquiring a second ultrasound dataset that represents the object in the first coordinate system at a second time;

means for locating the plurality of landmarks in the second ultrasound dataset to define a third coordinate system; and means for determining a second transform function from the first to the third coordinate systems for the second ultrasound dataset, the system further comprising:

means for displaying a first view of image data in the first ultrasound dataset in the second coordinate system using the first transform; and means for displaying a second view of image data in the second ultrasound dataset in the third coordinate system aligned with the first view using the second transform.

23. A system according to claim 22, further comprising: means for displaying the first and second views on a single display.

24. A system according to claim 22, wherein the first view of image data has an associated first time within a cycle associated with the object and the second view of image data has an associated second time within the cycle that is different than the first time.

25. A system according to claim 22, wherein the first and second views do not include any of the plurality of landmarks.

26. A system according to claim 22 further comprising: means for comparing the first and second views.

27. A system for aligning views of ultrasound data, the system comprising:

means for acquiring a first ultrasound dataset that represents an object in a first coordinate system at a first time;

means for locating a plurality of landmarks of the object in the first ultrasound dataset to define a second coordinate system;

means for determining a first transform function from the first to the second coordinate system for the first ultrasound dataset;

means for acquiring a second ultrasound dataset that represents the object in the first coordinate system at a second time;

means for locating the plurality of landmarks in the second ultrasound dataset to define a third coordinate system; and means for determining a second transform function from the first to the third coordinate systems for the second ultrasound dataset; wherein the means for locating the plurality of landmarks of the object in the first ultrasound dataset comprises means for locating a first one of the three landmarks in a first view of image data in the first ultrasound dataset and a second one of the three landmarks in a second view of image data in the first ultrasound dataset that is different from the first view.

28. A system for aligning views of ultrasound data, the system comprising:

means for acquiring a first ultrasound dataset that represents an object in a first coordinate system at a first time;

means for locating a plurality of landmarks of the object in the first ultrasound dataset to define a second coordinate system;

means for determining a first transform function from the first to the second coordinate system for the first ultrasound dataset;

means for acquiring a second ultrasound dataset that represents the object in the first coordinate system at a second time;

means for locating the plurality of landmarks in the second ultrasound dataset to define a third coordinate system; and means for determining a second transform function from the first to the third coordinate systems for the second ultrasound dataset, the system further comprising:

means for displaying a series of first view of image data in the first ultrasound dataset; and means for displaying a series of second views of image data in the second ultrasound dataset, wherein respective ones of the first views are aligned with respective ones of the second views.

29. A system for aligning views of ultrasound data, the system comprising:

means for acquiring a first ultrasound dataset that represents an object in a first coordinate system at a first time;

means for locating a plurality of landmarks of the object in the first ultrasound dataset to define a second coordinate system;

means for determining a first transform function from the first to the second coordinate system for the first ultrasound dataset;

means for acquiring a second ultrasound dataset that represents the object in the first coordinate system at a second time;

means for locating the plurality of landmarks in the second ultrasound dataset to define a third coordinate system; and means for determining a second transform function from the first to the third coordinate systems for the second ultrasound dataset, the system further comprising:

means for displaying a series of first views of image data from the first ultrasound dataset that correspond to respective locations in the object; and means for displaying a series of second views of image data from the second ultrasound dataset that correspond to the same locations in the object, wherein respective ones of the first and second views are aligned.

30. A system for aligning views of ultrasound data, the system comprising:

means for acquiring a first ultrasound dataset that represents an object in a first coordinate system at a first time;

means for locating a plurality of landmarks of the object in the first ultrasound dataset to define a second coordinate system;

means for determining a first transform function from the first to the second coordinate system for the first ultrasound dataset;

means for acquiring a second ultrasound dataset that represents the object in the first coordinate system at a second time;

means for locating the plurality of landmarks in the second ultrasound dataset to define a third coordinate system; and means for determining a second transform function from the first to the third coordinate systems for the second ultrasound dataset, wherein the first and second views are displayed simultaneously.

\* \* \* \* \*